(12) United States Patent
Keller

(10) Patent No.: US 7,303,586 B2
(45) Date of Patent: Dec. 4, 2007

(54) COUPLED KNEE PROSTHESIS WITH A ROTATIONAL BEARING

(75) Inventor: Arnold Keller, Kayhude (DE)

(73) Assignee: WALDERMAR LINK Gmbh & Co. KG, Hamburg (DE)

( * ) Notice: Subject to any disclaimer, the term of this patent is extended or adjusted under 35 U.S.C. 154(b) by 531 days.

(21) Appl. No.: 10/482,153

(22) Filed: Jun. 28, 2004

(65) Prior Publication Data
US 2004/0220676 A1 Nov. 4, 2004

(30) Foreign Application Priority Data
Jun. 27, 2001 (EP) .................................. 01115511

(51) Int. Cl.
A61F 2/38 (2006.01)
A61F 2/08 (2006.01)

(52) U.S. Cl. ................................. 623/20.29; 623/20.31

(58) Field of Classification Search ............ 623/20.14, 623/20.15, 20.24, 20.26, 20.27, 20.28, 20.29, 623/20.3, 20.31
See application file for complete search history.

(56) References Cited

U.S. PATENT DOCUMENTS

| | | | |
|---|---|---|---|
| 4,301,553 A | 11/1981 | Noiles | |
| 4,888,021 A | 12/1989 | Forte et al. | |
| 5,139,521 A * | 8/1992 | Schelhas | 623/20.25 |
| 5,370,701 A | 12/1994 | Finn | |
| 5,411,555 A * | 5/1995 | Nieder | 623/20.26 |
| 5,824,096 A * | 10/1998 | Pappas et al. | 623/23.39 |
| 6,099,570 A | 8/2000 | Livet et al. | |

FOREIGN PATENT DOCUMENTS

| | | | |
|---|---|---|---|
| DE | 23 34 265 B2 | 1/1975 | |
| DE | 26 36 816 A1 | 2/1977 | |
| DE | 2744710 | 4/1979 | |
| DE | 35-29-894 A1 | 3/1987 | |
| EP | 0 410 237 A1 | 1/1990 | |
| EP | 0 539 654 B1 | 5/1993 | |
| EP | 0 716 839 A1 | 6/1996 | |
| EP | 0 791 343 A2 | 8/1997 | |
| FR | 2 760 352 A1 | 9/1998 | |
| GB | 2129306 | * 11/1982 | .............. 623/20.29 |
| GB | 2-129-306 A | 5/1984 | |
| RU | 2-145-821 C1 | 2/2000 | |
| SU | 13521598 A1 | 11/1987 | |
| SU | 1803072 A1 | 3/1993 | |

* cited by examiner

Primary Examiner—Pedro Philogene
(74) Attorney, Agent, or Firm—Morrison & Foerster LLP

(57) ABSTRACT

A knee prosthesis includes a femoral component with condylar sliding surfaces which are rigidly interconnected, a tibial component provided with a tibial platform which is linked to it in a non-rotatable manner and has tibial sliding surfaces which cooperate with the condylar sliding surfaces, and a coupling device which forms a flexion bearing with the femoral component and a rotational bearing with the tibial component, the axis of said rotational bearing being inclined relative to the tibial direction. In order to achieve a more advantageous force distribution in the prosthesis and a restoring force upon rotation of the prosthesis parts, the prosthesis is configured such that the normal with respect to the area of the tibial sliding surfaces which cooperates with the condylar sliding surfaces and transmits most of the load in the extension position is less inclined relative to the tibial direction than is the axis of the rotational bearing, as seen in a side view or sagittal section.

4 Claims, 1 Drawing Sheet

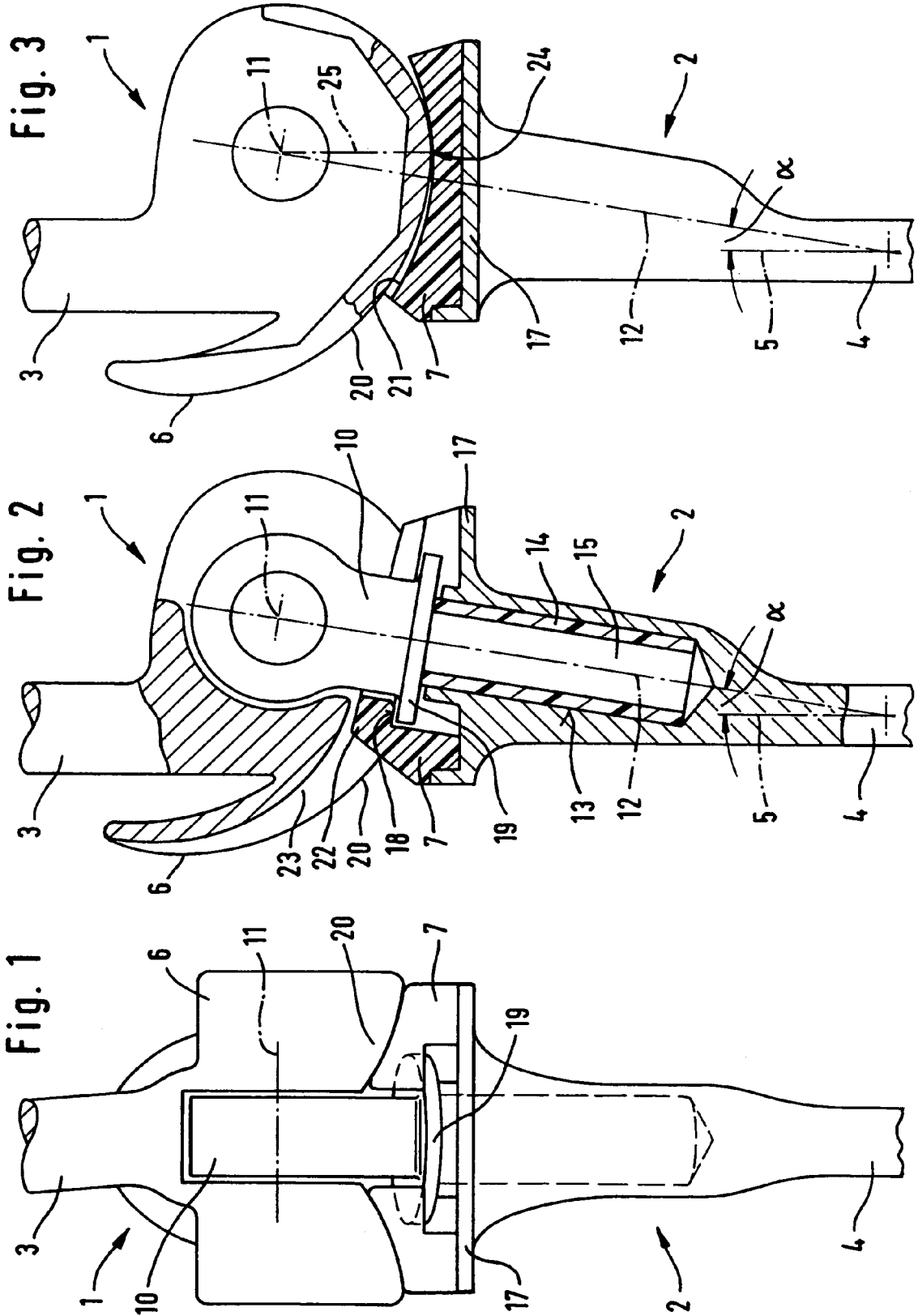

COUPLED KNEE PROSTHESIS WITH A ROTATIONAL BEARING

FIELD AND BACKGROUND OF THE INVENTION

Knee prostheses are known whose femoral and tibial components have different degrees of freedom relative to one another. The less the residual stability of the knee to be fitted with the prosthesis, the greater the stability that the prosthesis must provide and the smaller the number of degrees of freedom that can be given to the relative movement between the two components, and vice versa. The restriction on the degrees of freedom is achieved by a coupling device which acts between the femoral component and the tibial component. In accordance with the preamble of claim 1, the invention relates to that type of knee prosthesis equipped with a coupling device which forms a flexion bearing with the femoral component and a rotational bearing with the tibial component. The flexion bearing determines the movement of the components about the transverse axis during flexion. The rotational bearing, whose axis extends approximately parallel to the tibial direction, permits a certain rotation about the vertical axis.

The axial forces are transmitted from the condylar sliding surfaces of the femoral component to the tibial sliding surfaces cooperating with these on the top of the tibial platform. A distinction must be drawn here between two groups. In the prostheses of the first group, the rotational bearing comprises a platform which is rotatable relative to the tibial component and whose upper sliding surface cooperates only for the flexion movement with the condylar sliding surfaces of the femoral component (DE-B-2334265, DE-A-2636816, EP-A-716839, U.S. Pat. No. 4,888,021, U.S. Pat. No. 5,370,701). In the prostheses of the second group, the tibial platform is connected to the tibial component in a non-rotatable manner (U.S. Pat. No. 5,139,521, EP-B-410237, EP-B-539654, EP-A-791343). The invention concerns the second group. In this case, a relative movement between the femoral condylar sliding surfaces and the tibial sliding surfaces takes place not only during the flexion movement, but also during the rotation movement. To ensure, during the rotation movement, that both femoral condylar sliding surfaces maintain force-transmitting contact with the associated areas of the tibial sliding surface, it is considered necessary in the prior art for these areas of the tibial sliding surface to be oriented substantially perpendicular with respect to the axis of rotation. This applies at least to the flexion area in which most of the load transmission takes place. This is generally the extension position, or a flexion position close to the extension position. The requirement for substantially perpendicular orientation of the tibial sliding surfaces in this load-transmitting area relative to the axis of rotation has hitherto also been taken into consideration if the direction of the axis of rotation is inclined relative to the tibial axis, so that it is directed not at the ankle joint but at the foot surface (EP-B-410237). The tibial sliding surface is then inclined like the axis of rotation. It slopes down toward the rear. This has considerable drawbacks for the rotational bearing. The rearward inclination of the tibial sliding surface in fact leads to a horizontal force component which loads the rotational bearing with a moment about the horizontal axis and thus exposes it to increased wear.

SUMMARY OF THE INVENTION

The invention seeks to avoid this drawback by incorporating the features of the invention as disclosed herein.

Although the axis of rotation is inclined, the tibial sliding surface according to the invention is not provided with a corresponding inclination, which seems contradictory in terms of kinematics because, in the event of rotation, it precludes symmetrical force transmission via both condylar surfaces. What this achieves is, firstly, that the stated horizontal force component, and the excessive stressing of the rotational bearing caused by the latter, is avoided. Also, the invention has the advantage that a rotational movement of the prosthesis components is at all times associated with the generation of a restoring force. During rotation, one of the two contact points of the femoral condyles on the tibial sliding surface migrates forward, and the other migrates rearward. Since the tibial sliding surface is not perpendicular with respect to the axis of rotation, one of the two condylar contacts gains height, during this displacement, relative to the rotational bearing compared to the previous state. Its attempt to return, under loading, to the lower, previous state generates the restoring force.

An embodiment is preferred in which the tibial sliding surface extends approximately perpendicular with respect to the tibial direction. More precisely, the direction of the normal with respect to the tibial sliding surface is parallel to the tibial direction. This applies to the area of the tibial sliding surface at which most of the load transmission from the condylar sliding surface to the tibial sliding surface takes place in the extended state of the prosthesis. However, the inventive concept is also realized if the tibial sliding surface extends at a slight inclination, in particular if the angle between said normal and the tibial direction is not more than half as great as the angle between the axis of the rotational bearing and the tibial direction.

The fact that a restoring force is exerted on the rotated prosthesis components by the angle difference between the direction of the rotational bearing and said normal does not mean that further means for generating such a restoring force have to be avoided. In particular, a raised central rib can be provided, as is known (DE 2744710), between the two areas of the tibial sliding surface which cooperate with the two condylar sliding surface parts.

BRIEF DESCRIPTION OF THE DRAWINGS

The invention is explained in more detail below with reference to the drawing which depicts an advantageous illustrative embodiment, and in which:

FIG. 1 shows a dorsal view,

FIG. 2 shows a sectional view, and

FIG. 3 shows a side view of the prosthesis.

DETAILED DESCRIPTION OF THE INVENTION

The prosthesis comprises a femoral part 1 and a tibial part 2 which are to be anchored respectively in the femur and in the tibia via stems 3 and 4, respectively. The direction 5 of the stem 4 indicates the tibial direction. The load is transmitted from the femoral part 1 to the tibial part 2 in each flexion position by femoral runners 6 and a tibial platform 7. For stabilizing purposes, the femoral part and tibial part are connected to one another by an intermediate part 10 which, as coupling device, forms a hinge with the femoral part 1, the axis 11 of which hinge coincides with the flexion axis, and forms, with the tibial part 2, a rotational bearing with axis of rotation 12. The rotational bearing consists of a pin 15 of the intermediate part 10 and of a bore 13 in the tibial part, which bore 13 has a slide bushing 14, for example of polyethylene, which receives the pin 15 with a sliding fit. In the sagittal plane, the axis of rotation 12 encloses, with the tibial direction 5 of the prosthesis, an angle α which is 9° in the example shown (generally between 4° and 15°).

The runners 6 of the femoral part take the place of the natural condyles. The sliding surfaces 20 formed by them are therefore referred to as condylar sliding surfaces. In side view, they can be formed as an arc of a circle. In this case, their axis of curvature coincides with the flexion axis 11. They can also be made polycentric for better approximation to the natural conditions.

The tibial platform 7 is held rigidly on a plate 17 of the tibial part. It is also preferably secured thereon against lifting (for example by screws). It comprises an undercut 18 which, cooperating with a collar 19 of the intermediate part 10, ensures that the pin 12 remains in the rotational bearing.

At its top, the tibial platform 7 forms a tibial sliding surface 21. It forms a sliding surface area for each condylar sliding surface 20. Between these, the tibial platform forms a raised, ridge-like area 22 which protrudes into the intercondylar notch 23 of the femoral part.

In the side view or sagittal section, the tibial sliding surface 21 of the tibial platform 7 is expediently shaped as a concave depression in order to approximate more or less to the shape of the condylar sliding surfaces 20. The surface contact pressure is thereby reduced. Complete congruence is of course possible, but in most cases it is neither necessary nor desired. In the frontal section, by contrast, considerable agreement of shape of the condylar and tibial sliding surfaces 20, 21 is desired, it being assumed that they take up their neutral position with respect to the axis of rotation 12, which position corresponds to the extension state of the leg.

If the tibial platform 7 is arranged securely on the tibial part 2, the relative position of the condylar and tibial sliding surfaces 20, 21 is determined by the flexion axis 11. If the radius of curvature of the tibial sliding surface 21 is greater than that of the condylar sliding surface 20, then the geometric relationships are chosen such that the theoretical geometrical point of contact in the non-rotated state of the prosthesis parts lies at an area of the tibial sliding surface whose normal (i.e. a line perpendicular to the surface of the area in question) extends approximately parallel to the tibial direction 5. This area and the associated normal are shown in FIG. 3 by reference numbers 24 and 25.

If (departing from the embodiment shown) the radii of curvature of the condylar and tibial sliding surfaces 20, 21 are identical in sagittal section, the load transmission is not distributed across the whole theoretical contact surface. Rather, an area of main force transmission is likewise formed. This generally has a horizontal setting in the extension and standing position. Here once again, therefore, the normal extends approximately parallel to the tibial direction.

If (departing from the embodiment shown), the tibial platform 7 can be moved forward and backward relative to the tibial part 1 on a guide plane during the flexion movement, the platform in each case takes up a position such that the tibial sliding surface at the point of greatest force transmission extends approximately parallel to the guide plane of the tibial platform. The normal with respect to the main load-transmitting area is thus perpendicular to the guide surface.

In all these cases, the invention requires that the construction be made such that, in side view, the normal with respect to the main load-transmitting area is inclined less relative to the tibial direction than is the axis of the rotational bearing. If the tibial direction is imagined as being vertical, the tibial sliding surface should therefore be approximately horizontal at this area.

If the prosthesis components 1 and 2 are not turned relative to the axis 12 (neutral position), as is generally the case in the extension position, both condylar sliding surfaces lie, transmitting forces, on the associated areas of the tibial sliding surface. When rotation about the axis 12 takes place between the prosthesis parts 1 and 2 and the sliding surfaces 20 and 21, there is a forward/backward relative displacement of the sliding surface areas lying on one another at area 24. If the normal with respect to this area were to extend parallel to the axis of rotation 12, as is known, there would be no substantial change in the height of the affected area of the condylar sliding surface 20 in relation to the rotational bearing. However, because, according to the invention, the normal 25 with respect to this area has a direction other than the axis of rotation 12, the sliding surfaces 20, 21 at the area concerned are inclined relative to the circumferential direction. The result of this is that, on one condylar side, lifting of the condylar sliding surface 20 relative to the tibial component of the prosthesis is forced. Under loading, the arrangement therefore seeks to return to the neutral rotation position.

The invention also has the advantage that, in most loading situations, the direction of the normal 25 corresponds approximately to the load direction. The development of transversely extending forces and resulting bending moments acting on the rotational bearing 13, 14, 15 are therefore less than would be the case if the concerned area of the sliding surfaces were to be inclined like the axis of rotation.

The invention claimed is:

1. A knee prosthesis comprising:
    a femoral component comprising interconnected condylar sliding surfaces,
    a tibial component comprising a non-rotatable tibial platform tibial sliding surfaces which are configured to cooperate with the condylar sliding surfaces, and
    a coupling device which forms a flexion bearing in combination with the femoral component and a rotational bearing in combination with the tibial component, the rotational bearing having a rotational bearing axis that is inclined relative to a tibial direction,
    wherein a line normal to that area of the tibial sliding surfaces which cooperates with the condylar sliding surfaces and transmits a load in an extension position is less inclined relative to the tibial direction than is the rotational bearing axis, as seen in a side view or sagittal section.

2. The knee prosthesis as claimed in claim 1, wherein an angle between said normal line and the tibial direction is not more than half as great as an angle (α) between the rotational bearing axis and the tibial direction.

3. The knee prosthesis as claimed in claim 2, wherein said normal line is approximately parallel to the tibial direction.

4. The knee prosthesis as claimed in one of claims 1 through 3, wherein one tibial sliding surface is elevated in an intercondylar area.

* * * * *

UNITED STATES PATENT AND TRADEMARK OFFICE
CERTIFICATE OF CORRECTION

| | |
|---|---|
| PATENT NO. | : 7,303,586 B2 |
| APPLICATION NO. | : 10/482153 |
| DATED | : December 4, 2007 |
| INVENTOR(S) | : Arnold Keller |

It is certified that error appears in the above-identified patent and that said Letters Patent is hereby corrected as shown below:

<u>On the cover page, in section (73) Assignee:</u>

Please replace "WALDERMAR LINK Gmbh & Co. KG" with

--WALDEMAR LINK GmbH & Co. KG--.

Signed and Sealed this

Sixth Day of May, 2008

JON W. DUDAS
*Director of the United States Patent and Trademark Office*